(12) United States Patent
Wang et al.

(10) Patent No.: US 10,767,482 B2
(45) Date of Patent: Sep. 8, 2020

(54) RESCUE CAPSULE FOR SHELTER IN TUNNEL CONSTRUCTION

(71) Applicant: CHANG'AN UNIVERSITY, Xi'an, ShaanXi (CN)

(72) Inventors: Yaqiong Wang, ShaanXi (CN); Fuxiang Chen, ShaanXi (CN); Zhifeng Wang, ShaanXi (CN); Rui Ren, ShaanXi (CN); Junfeng Tian, ShaanXi (CN); Shichao Zhang, ShaanXi (CN); Mengke Zhang, ShaanXi (CN); Haotian Guo, ShaanXi (CN); Zhanyi Chang, ShaanXi (CN); Yiwei Cui, ShaanXi (CN); Linjin Gong, ShaanXi (CN); Mingrui Luo, ShaanXi (CN)

(73) Assignee: CHANG'AN UNIVERSITY, Xi'an (CN)

( * ) Notice: Subject to any disclaimer, the term of this patent is extended or adjusted under 35 U.S.C. 154(b) by 0 days.

(21) Appl. No.: 16/667,568

(22) Filed: Oct. 29, 2019

(65) Prior Publication Data
US 2020/0131907 A1  Apr. 30, 2020

(30) Foreign Application Priority Data
Oct. 31, 2018 (CN) .......................... 2018 1 1291140

(51) Int. Cl.
*E21F 11/00* (2006.01)
*A61L 9/00* (2006.01)
(Continued)

(52) U.S. Cl.
CPC ................ *E21F 11/00* (2013.01); *A61L 9/00* (2013.01); *G01N 33/004* (2013.01); *G01N 33/0047* (2013.01); *F41H 5/263* (2013.01)

(58) Field of Classification Search
CPC .......... E21F 11/00; A61L 9/00; G01N 33/004; G01N 33/0047; F41H 5/263
(Continued)

(56) References Cited

U.S. PATENT DOCUMENTS

| | | | | |
|---|---|---|---|---|
| 2,343,353 A | * | 3/1944 | Wise ...................... | H04L 12/04 358/439 |
| 2,551,750 A | * | 5/1951 | Liskey, Jr. .............. | B63B 19/26 114/201 R |

(Continued)

FOREIGN PATENT DOCUMENTS

| | | | |
|---|---|---|---|
| CN | 202181820 U | * | 4/2012 |
| CN | 202451208 U | | 9/2012 |

(Continued)

*Primary Examiner* — Jeanette E Chapman
(74) *Attorney, Agent, or Firm* — Wayne & Ken, LLC; Tony Hom

(57) ABSTRACT

Provided is a rescue capsule for shelter in tunnel construction, relating to lifesaving equipment. The rescue capsule includes a housing. A cavity of the housing includes an equipment compartment which is located at an upper portion of the cavity and a passenger compartment which is located at a lower portion of the cavity. An exterior of the housing is provided with an external skeleton. The exterior of the housing is further provided with an external indicating sign and an external rescue indicator. The housing is further provided with an explosion-proof sealing door. An oxygen cylinder, a power supply, a maintenance box, a first air purifier and a medical box are provided in the equipment compartment. Areas where the maintenance box and the medical box of the equipment compartment are provided communicate with the passenger compartment.

10 Claims, 6 Drawing Sheets

(51) Int. Cl.
*G01N 33/00* (2006.01)
*F41H 5/26* (2006.01)

(58) Field of Classification Search
USPC .......................................................... 52/28
See application file for complete search history.

(56) References Cited

U.S. PATENT DOCUMENTS

| | | | | |
|---|---|---|---|---|
| 3,060,465 | A | * | 10/1962 | Carstensen ............... B63C 9/06 441/87 |
| 3,416,750 | A | * | 12/1968 | Young ..................... B64G 1/58 244/159.1 |
| 3,478,464 | A | * | 11/1969 | Appel .................... A63H 33/00 446/9 |
| 4,297,757 | A | * | 11/1981 | Palemon Camu ........ B63C 9/06 114/138 |
| 4,822,311 | A | * | 4/1989 | Doerffer .................. B63C 9/06 441/87 |
| D310,058 | S | * | 8/1990 | Thompson ................... D12/300 |
| 8,530,756 | B1 | * | 9/2013 | Winch ................. H05K 9/0001 174/382 |
| 8,534,215 | B2 | * | 9/2013 | Lee .......................... B63C 9/06 114/344 |
| 9,845,610 | B2 | * | 12/2017 | Scott, IV .................. E04H 9/14 |
| 2006/0111749 | A1 | * | 5/2006 | Westenskow .......... G09B 19/00 607/5 |
| 2012/0247034 | A1 | * | 10/2012 | Wystup ................. E04B 1/3448 52/65 |
| 2013/0014791 | A1 | * | 1/2013 | Hill ........................ E04H 9/145 135/93 |
| 2014/0020946 | A1 | * | 1/2014 | Winch ................. H05K 9/0015 174/353 |

FOREIGN PATENT DOCUMENTS

| | | | |
|---|---|---|---|
| CN | 203050767 | U * | 7/2013 |
| CN | 205400798 | U * | 7/2016 |
| CN | 105931527 | A | 9/2016 |
| CN | 205677284 | U * | 11/2016 |
| CN | 206950479 | U * | 2/2018 |
| GB | 1378561 | A | 12/1974 |

* cited by examiner

RESCUE CAPSULE FOR SHELTER IN TUNNEL CONSTRUCTION

CROSS-REFERENCE TO RELATED APPLICATIONS

This application claims the benefit of priority from Chinese Patent Application No. 201811291140.3, filed on Oct. 31, 2018. The content of the aforementioned application, including any intervening amendments thereto, is incorporated herein by reference in its entirety.

TECHNICAL FIELD

The present application relates to lifesaving equipment, and more particularly to a rescue capsule for shelter in tunnel construction.

BACKGROUND OF THE INVENTION

China has a vast stretch of territory, of which mountains and heavy hills account for about 75%. Tunnels are inevitably required to be constructed to allow roads to cross mountainous or hilly areas. The tunnel is a basic form for utilizing the underground space, and is an important component for forming transportation networks, such as railways, highways and urban subways. China has made a remarkable achievement based on the mature drilling techniques such as the drill-blasting method, drilling with tunnel boring machines and shield tunneling method, etc., tunnel construction and support technique adapted to geological conditions and modern operation and management modes. Nowadays, China has the rapidest development speed, the largest number and the most complicated construction conditions in tunnels and underground engineering. However, the accumulation and mastery of key techniques of tunnel constructions in China are still in the primary stage, and resolutions for accidents, such as collapses, water inrush and burst, hole shrinkage and support cracking are under-developed, which seriously threatens the safety of front-line construction workers and even causes severe casualties and property loses. The delayed blocking collapse of the tunnel is the most dangerous accident among those construction accidents threatening the safety of construction workers. During such tunnel accident, the construction workers cannot escape from dangerous areas in time, which leads to severe casualties.

The conventional method for solving the delayed blocking collapse is to place escape pipes on the bottom of tunnel sidewall. In principle, such escape pipe may help those front-line construction workers to escape from accidents, but connection of round pipes are not convenient, and multiple round pipes are connected via sleeve pipes, so connecting portions are easy to be broken. According to long-term construction site investigation, due to the disadvantages of too much interfaces, unsealing and inconvenient storage and transportation, the round pipes used at the construction site are often found to be placed outside the tunnel. When the blocking collapse happens in tunnels, the escape pipes are a hidden threat for the safety of the construction workers, because the outside escape pipes which cannot be used for the emergency escape may even hamper on-site rescues. Therefore, when tunnels are subjected to an accident, such tunnel escape pipes have a certain impact on the escape of the construction workers inside the tunnel and the rescue of the rescue workers outside the tunnel.

SUMMARY OF THE INVENTION

In view of above defects, the present invention provides a rescue capsule for shelter in tunnel construction, by which a safe shelter is provided for construction workers who have not evacuated to safe areas when the tunnel is in danger.

The present adopts the following technical solutions to achieve the above object.

Provided is a rescue capsule for shelter in tunnel construction, comprising a housing which is hollow; a cavity of the housing comprises an equipment compartment which is located at an upper portion of the cavity and a passenger compartment which is located at a lower portion of the cavity; an exterior of the housing is provided with an external skeleton.

The exterior of the housing is further provided with an external indicating sign and an external rescue indicator.

The housing is further provided with an explosion-proof sealing door.

An oxygen cylinder, a power supply, a maintenance box, a first air purifier, and a medical box are provided in the equipment compartment; areas where the maintenance box and the medical box of the equipment compartment are provided communicate with the passenger compartment.

A light, a second air purifier, a gas sensor, a communication device and a survival support device are provided in the passenger compartment. The light, the first air purifier, the second air purifier, the gas sensor and the communication device are respectively connected to the power supply. The oxygen cylinder and the gas sensor are respectively connected to the second air purifier.

The housing comprises an inner heat-preserving layer and an outer pressure-resistant layer.

The gas sensor comprises a CO sensor, a $CO_2$ sensor, and a $CH_4$ sensor.

A switch is respectively provided between the power supply and the light, the first air purifier and the second air purifier.

A seat is provided at a lower portion of the passenger compartment, and the survival support device is arranged below the seat.

The explosion-proof sealing door is provided with a bulletproof glass window and a handle.

A reflective coating is coated on the external indicating sign.

The external indicating sign is respectively arranged on two sides of the explosion-proof sealing door of the housing, where the external indicating sign is an indicating arrow, and respective indicating signs of two sides of the explosion-proof sealing door are directed to the explosion-proof sealing door.

The rescue capsule is respectively arranged at left and right sides of a lower portion of a tunnel excavation trolley.

The communication device is a wireless communication device or a wired communication device. When the communication device is a wired communication device, a communication interface is provided on the housing. The communication interface is connected to the communication device and an external communication cable outside the rescue capsule.

Compared to the prior art, the present invention has the following advantages.

The rescue capsule of the present invention is divided into an equipment compartment which is located at an upper portion of the cavity and a passenger compartment which is located at a lower portion of the cavity, which effectively saves the space and improve the space utilization. At the same time, the exterior of the housing is provided with an external indicating sign and an external rescue indicator. When the tunnel is in danger, the external rescue indicator is turned on, so that the construction workers can easily find locations of the rescue capsule in time. The external indicating sign can safely and accurately guide the construction workers to find the explosion-proof sealing door in time, and then evacuate them to the rescue capsule to avoid the danger, thus guaranteeing the safety of the construction workers.

The equipment compartment is provided with an oxygen cylinder, a power supply, a maintenance box, a first air purifier, and a medical box. The locations of the maintenance box and the medical box of the equipment compartment communicate with the passenger compartment, so that the maintenance for the secure capsule and the corresponding medical treatment are available when the tunnel construction workers enters the rescue capsule in emergency circumstances, thereby ensuring the safety of the sheltering workers. At the same time, the normal operation of the tunnel rescue capsule can be ensured, because the first air purifier of the equipment compartment is mainly for supplying air for the passenger compartment to ensure the air flow in the passenger compartment, so that the passenger compartment has good air qualities.

The passenger compartment is provided with a light, a second air purifier, a gas sensor, a communication device and a survival support device, which are mainly used to ensure the normal life of the tunnel construction workers after they are evacuated into the tunnel rescue capsule. The light is mainly for the evacuation of tunnel construction workers, and the second air purifier of the passenger compartment is mainly to maintain the air quality in the passenger compartment of the rescue capsule in a normal state. The gas sensor is mainly for monitoring harmful gases in the passenger compartment of the rescue capsule. When the concentration of harmful gases in the passenger compartment reaches the set standard, the second air purifier will carry out corresponding treatment to allow the gas concentration in the passenger compartment to reach a normal standard. The communication device is mainly to ensure the communication between the sheltering personnel and the outside world, enabling outside rescuers to take effective measures to aid the sheltering personnel. The survival support device mainly comprises foods and water which are used for maintaining the normal life of the sheltering personnel in the passenger compartment when waiting for the external rescue.

Compared to the conventional tunnel escape pipelines, the rescue capsule of the present invention is provided with an outer skeleton on the outer surface of the housing, and the outer skeleton can be closely adhered to the whole structure of the housing of the rescue capsule to share the external load impact, thereby protecting the safety of the construction workers. Moreover, the explosion-proof sealing door is further provided on the housing for the entering and exiting of personnel, so the rescue capsule of the invention has great advantages in terms of the sealing of the device, which protects the personal safety of the internal personnel to a large extent. The rescue capsule of the present invention is provided in the tunnel for the first time, which greatly combines the practical situations of existing tunnels during the construction and adopts corresponding devices for protecting the personal safety of the tunnel construction workers. Such rescue capsule is advanced in safety of the tunnel construction, and better shows the people-oriented principle. The rescue capsule of the present invention is convenient and safe to operate, and is reusable. Moreover, it is convenient to be assembled, debugged and disassembled. Therefore, compared with the conventional tunnel escape pipelines, the rescue capsule of the present invention is more practical.

Further, the rescue capsule is arranged at left and right sides of the lower portion of the tunnel excavation trolley, which effectively utilizes the space of the tunnel excavation trolley. Moreover, the rescue capsule moves with the excavation trolley, which ensures the safe distance which will not exceed 30 m between the rescue capsule and the construction workers. The conventional tunnel escape pipelines cannot be laid in time, and the construction workers cannot be evacuated in time when tunnels are in danger, so severe accidents will happen. However, such accidents are avoided when using the rescue capsule of the present invention.

Figure 1:
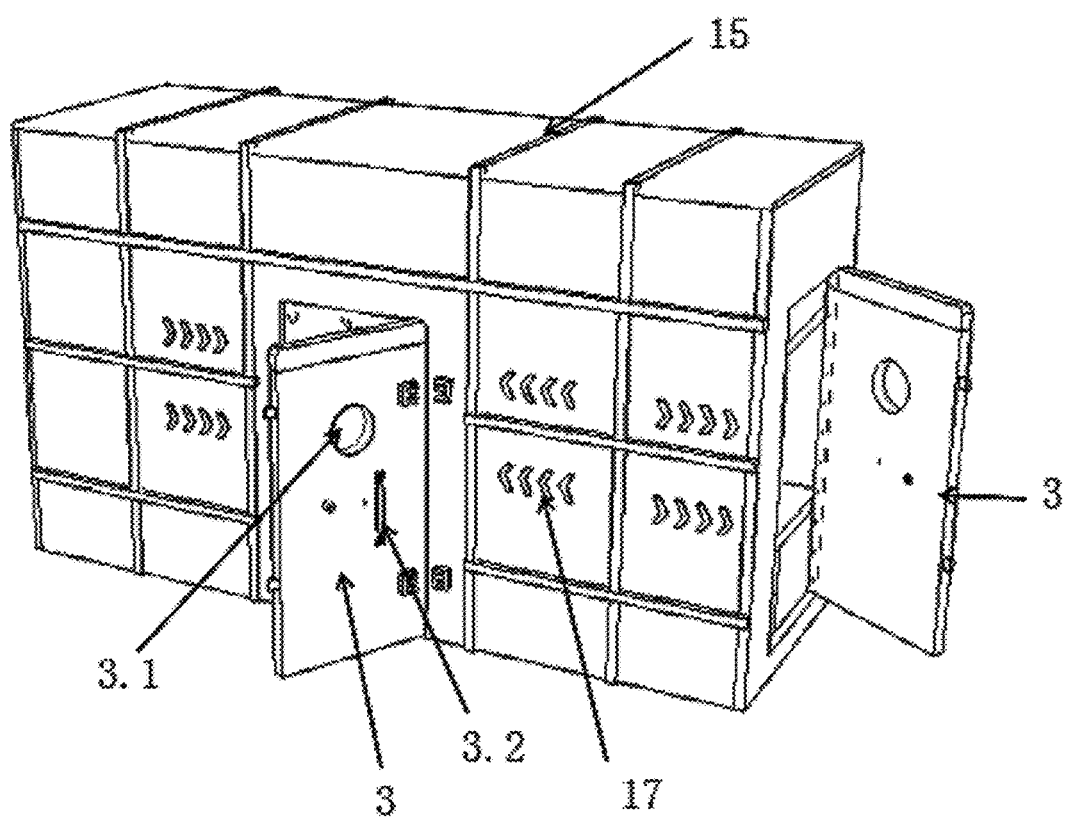
FIG. 1 is a schematic diagram of a rescue capsule according to the present invention.

In the drawings: 1, equipment compartment; 2, passenger compartment; 3, explosion-proof sealing door; 3.1, bullet-proof glass window; 3.2, handle; 4, light; 5, oxygen cylinder; 6, power supply; 7-A, first air purifier; 7-B, second air purifier; 8, air sensor; 9, communication device; 10, survival support device; 11, outer pressure-resistant layer; 12, inner heat-preserving layer; 13, maintenance box; 14, medical box; 15, external skeleton; 16, seat; 17, external indicating sign; 18, external rescue indicator; 19, communication interface; 20, excavation trolley; 21; rescue capsule; 22, top plate of passenger compartment.

DETAILED DESCRIPTION OF EMBODIMENTS

The present invention will be further described with reference to the accompanying drawings.

Figure 3:
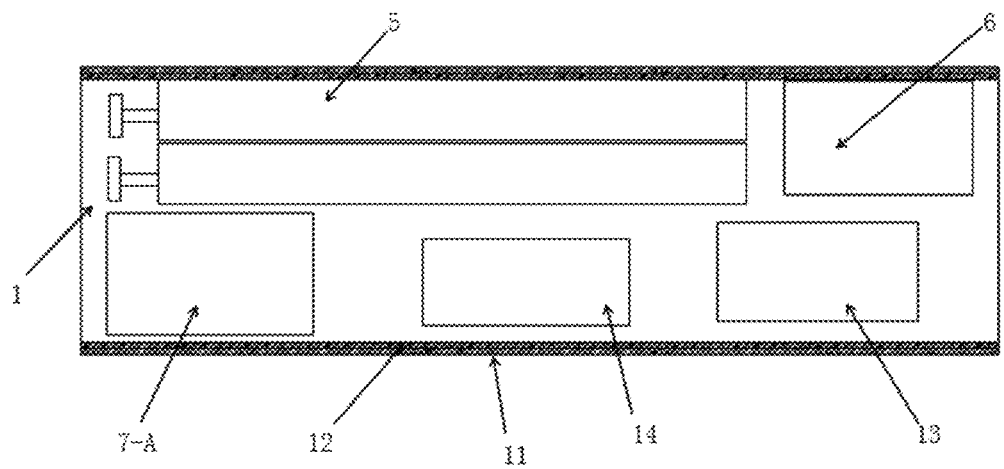
FIG. 3 is a schematic diagram of an equipment compartment which is an upper portion of the rescue capsule according to the present invention.
Figure 4:
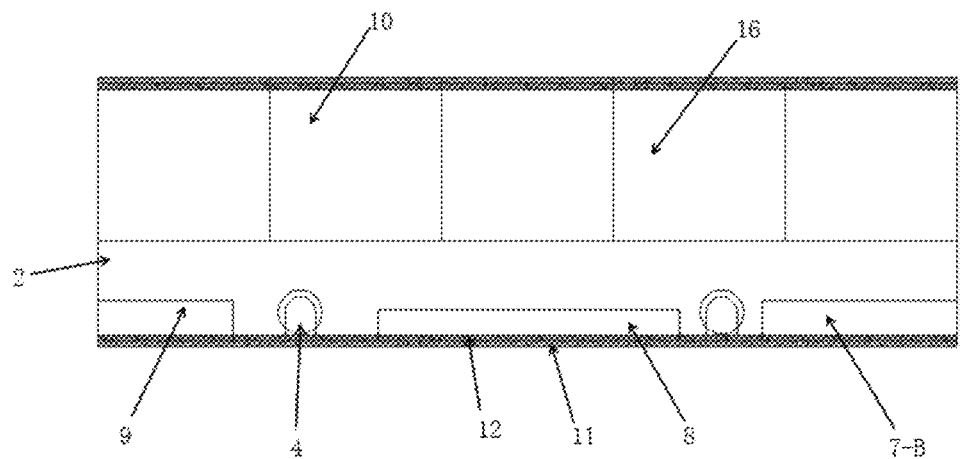
FIG. 4 is a schematic diagram of a passenger compartment which is a lower portion of the rescue capsule according to the present invention.
Figure 5:
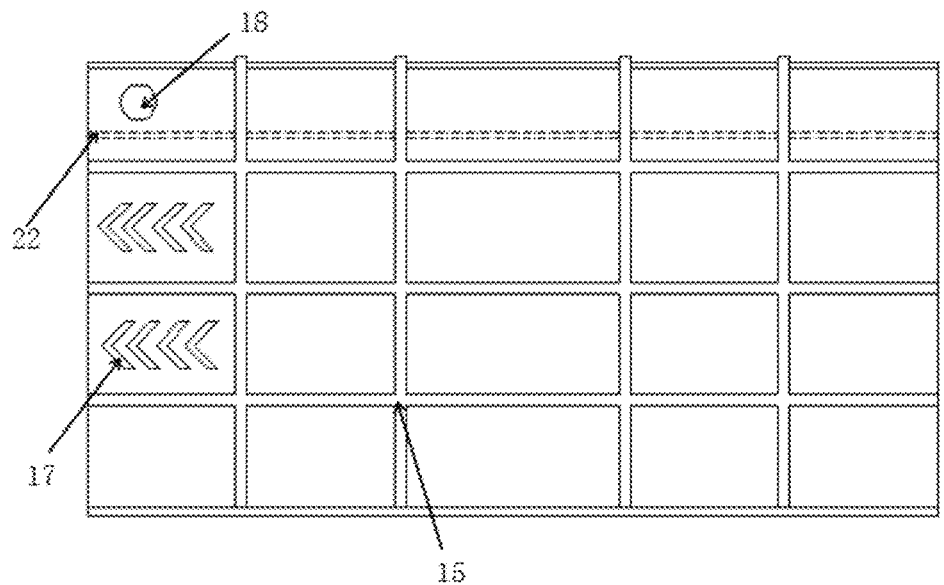
FIG. 5 is a schematic diagram showing an arrangement of an external indicating sign and an external rescue indicator of the rescue capsule according to the present invention.
Figure 6:
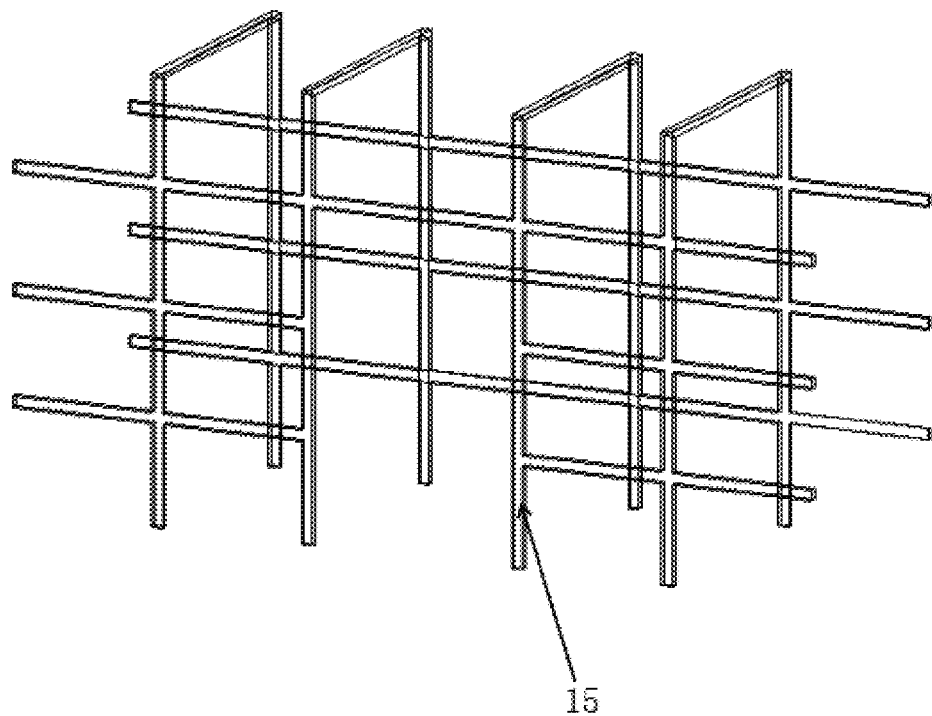
FIG. 6 is a schematic diagram of an external skeleton of the rescue capsule according to the present invention.
Figure 7:
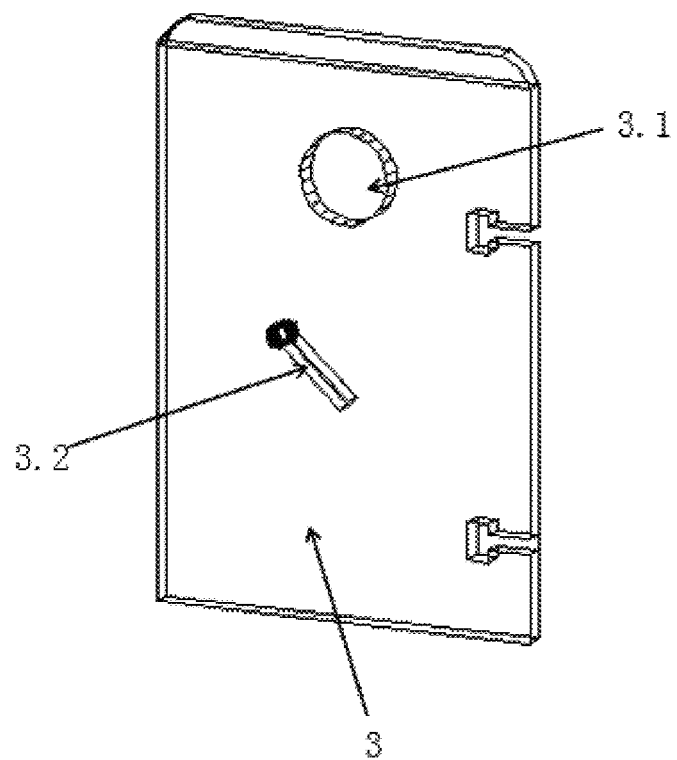
FIG. 7 is a schematic diagram showing an arrangement of an explosion-proof sealing door of the rescue capsule according to the present invention.
Figure 8:
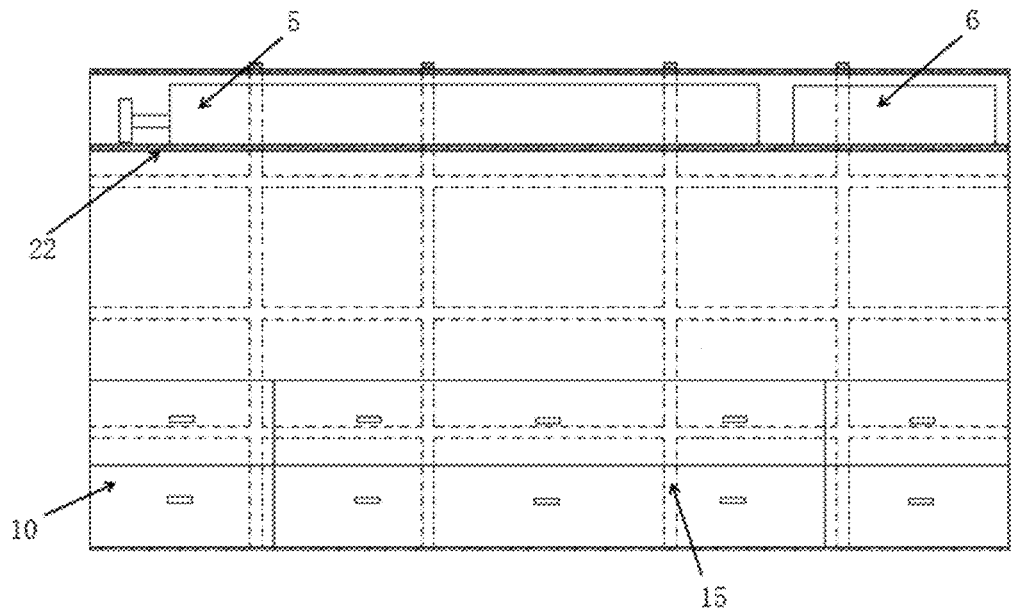
FIG. 8 is a cross section of the rescue capsule according to the present invention.

As shown in FIG. 1, illustrated is a rescue capsule for shelter in tunnel construction, comprising a housing which is hollow. As shown in FIG. 8, a cavity of the housing comprises an equipment compartment 1 (FIG. 3) which is located at an upper portion of the cavity and a passenger compartment 2 (FIG. 4) which is located at a lower portion of the cavity 22 is a top plate of the passenger compartment. An exterior of the housing is provided with an external skeleton 15 (FIGS. 1, 5, 6, 8 and 9). The exterior of the housing is further provided with an external indicating sign 17 and an external rescue indicator 18 (as shown in FIGS. 1 and 5). The external rescue indicator 18 is mainly to ensure that the external rescue indicator is turned on when the tunnel is in danger, so that the construction workers can easily find locations of the tunnel rescue capsule in time. The housing is further provided with an explosion-proof sealing door 3 (FIGS. 1 and 7). As shown in FIGS. 3 and 8, an oxygen cylinder 5, a power supply 6, a maintenance box 13, a first air purifier 7-A, and a medical box 14 are provided in the equipment compartment 1. Areas where the maintenance box 13 and the medical box 14 of the equipment compartment 1 are provided communicate with the passenger compartment 2, so that the maintenance for the secure capsule and the corresponding medical treatment are available when the tunnel construction workers enters the rescue capsule in emergency circumstances, thereby ensuring the safety of the sheltering workers. At the same time, the normal operation of the tunnel rescue capsule can be ensured. As shown in FIGS. 4 and 8, a light 4, a second air purifier 7-B, a gas sensor 8, a communication device 9 and a survival support device 10 are provided in the passenger compartment 2. The light 4, the first air purifier 7-A, the second air purifier 7-B, the gas sensor 8 and the communication device 9 are respectively connected to the power supply 6. The oxygen cylinder 5 and the gas sensor 8 are respectively connected to the second air purifier 7-B. The survival support device 10 mainly comprises foods and water which are used for maintaining the normal life of the sheltering personnel in the passenger compartment when waiting for the external rescue.

Figure 2:
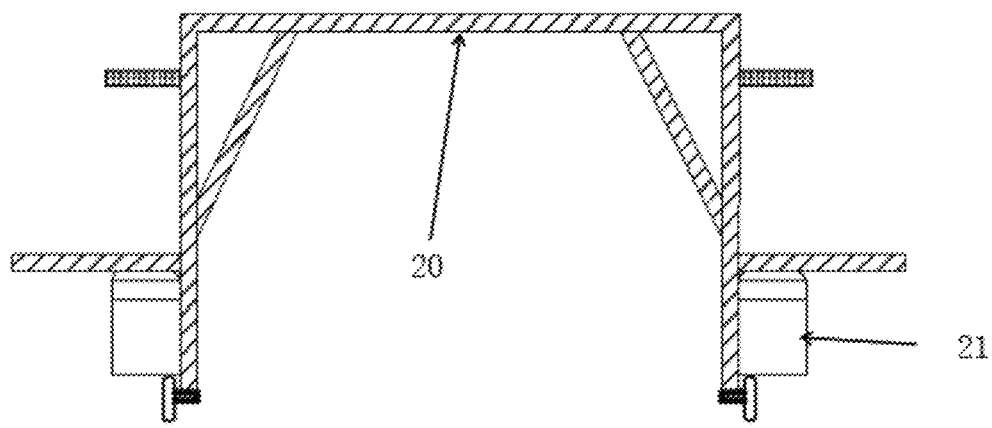
FIG. 2 is a schematic diagram showing an arrangement of the rescue capsule at an excavation trolley according to the present invention.
Figure 9:
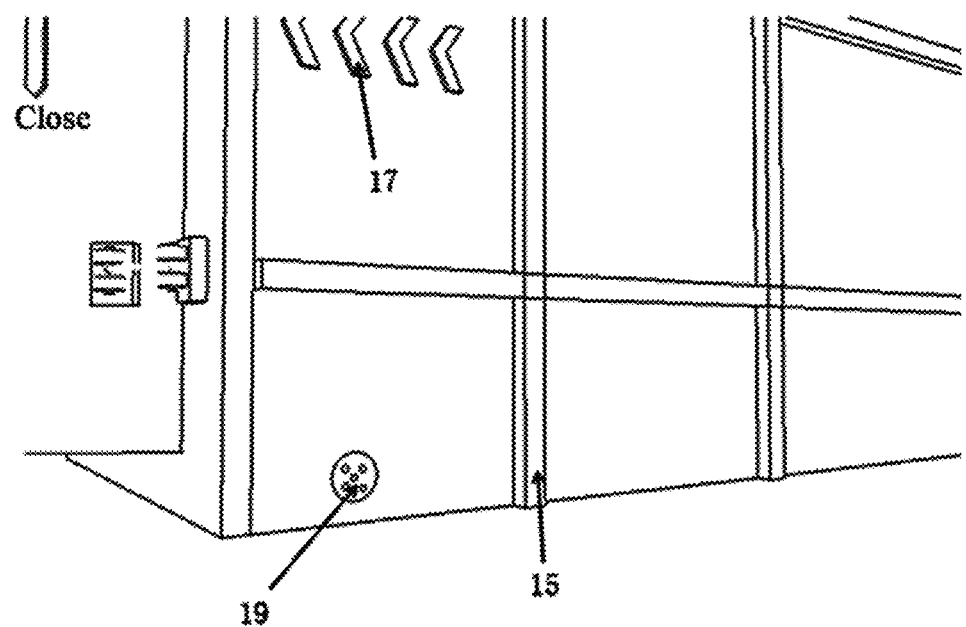
FIG. 9 is a schematic diagram showing a communication interface of the rescue capsule which is for connecting an external power supply.

In some embodiments, as shown in FIGS. 3-4, the housing comprises an inner heat-preserving layer 12 and an outer pressure-resistant layer 11. The gas sensor 8 comprises a CO sensor, a $CO_2$ sensor, and a $CH_4$ sensor. A switch is respectively provided between the power supply 6 and the light 4, the first air purifier 7-A and the second air purifier 7-B. A seat 16 is provided at a lower portion of the passenger compartment 2, and the survival support device 10 is arranged below the seat 16. As shown in FIGS. 1 and 7, the explosion-proof sealing door 3 is provided with a bullet-proof glass window 3.1 and a handle 3.2. A reflective coating is coated on the external indicating sign 17. As shown in FIG. 1, the external indicating sign 17 is respectively arranged on two sides of the explosion-proof sealing door 3 of the housing, where the external indicating sign 17 is an indicating arrow, and respective indicating signs 17 of two sides of the explosion-proof sealing door 3 are directed to the explosion-proof sealing door 3. The external indicating signs can help the construction workers to easily find a location of the explosion-poof sealing door 3 in time, so that the construction workers can enter the rescue capsule 21 for sheltering. As shown in FIG. 2, the rescue capsule for shelter in tunnel construction is respectively arranged at left and right sides of a lower portion of a tunnel excavation trolley 20. The communication device 9 is a wireless communication device or a wired communication device. As shown in FIG. 9, when the communication device 9 is a wired communication device, a communication interface 19 is provided on the housing. The communication interface is connected to the communication device 9 and an external communication cable outside the rescue capsule.

The light 4, the second air purifier 7-B, the gas sensor 8 and the communication device 9 are mainly arranged on a front panel of the passenger compartment 2. A lower part of the passenger compartment 2 is mainly provided with seats 16, where five seats 16 are provided for the construction workers. The survival support device 10 is provided below the seats 16 and is mainly provided with foods, water and a resuscitator which can ensure that the tunnel construction workers can live in the rescue capsule for a certain period when the tunnel is in danger.

The rescue capsule of the present invention is mainly used for providing a safe evacuation site for the construction workers who have not been evacuated to a safe area when the tunnel is in danger. The rescue capsules are mainly arranged on left and right sides of a lower part of the tunnel excavation trolley, which can effectively save space and utilize spaces on the left and right sides of the tunnel excavation trolley. At same time, the existing escape pipeline may not be installed in time, thus causing unforeseen accidents, which is effectively avoided by the present invention. The rescue capsule can move with the excavation trolley simultaneously, which can guarantee a distance which is within 30 m between the rescue capsule and the front-line construction workers.

The cavity of the rescue capsule is divided into upper and lower portions, and the housing of the rescue capsule comprises two layers. The outer pressure-resistant layer 11 is made of pressure-resistant materials and has a thickness of 8 mm, and is mainly used for resisting the impact from falling rocks during the collapsing of tunnels. The inner heat-preserving layer 12 is made of heat-insulating materials, and has a thickness of 3.5 mm. Moreover, the rescue capsule of the present invention is provided with an outer skeleton on the outer surface of the housing, and the outer skeleton can be closely adhered to the whole structure of the housing of the rescue capsule to share the external load impact, thereby protecting the safety of the construction workers.

As shown in FIG. 2, the equipment compartment 1 and the passenger compartment 2 of the rescue capsule 21 of the present invention are assembled. After assembled, the rescue capsule integrates with left and right sides of the excavation trolley 20, and is connected to the external communication cable via the communication interface 19, and then the installation of the rescue capsule is completed. When the tunnel encounters a sudden accident, the tunnel construction workers will enter the tunnel rescue capsule with the help of the external rescue indicator 18 and the external indicating sign 17, and then turn on the power supply, so that the rescue capsule can work normally while waiting for external rescue.

The rescue capsule of the invention integrates the requirements of conventional tunnel rescue equipment, and is convenient to use, practical and economical. The conventional rescue pipelines are not mounted in time, leading to the expansion of the danger, which is avoided in the present invention because the rescue capsule moves with the tunnel excavation trolley 20 simultaneously. The rescue capsule effectively overcomes the problem that construction workers cannot be evacuated to safe areas in time when encountering sudden tunnel accidents such as blocking collapse.

We claim:

1. A rescue capsule for shelter in tunnel construction, comprising a housing which is hollow;
   wherein a cavity of the housing comprises an equipment compartment which is located at an upper portion of the cavity and a passenger compartment which is located at a lower portion of the cavity; an exterior of the housing is provided with an external skeleton;
   the exterior of the housing is further provided with an external indicating sign and an external rescue indicator;

the housing is further provided with an explosion-proof sealing door;

an oxygen cylinder, a power supply, a maintenance box, a first air purifier and a medical box are provided in the equipment compartment; areas where the maintenance box and the medical box of the equipment compartment are provided communicate with the passenger compartment; and a light, a second air purifier, a gas sensor, a communication device and a survival support device are provided in the passenger compartment; the light, the first air purifier, the second air purifier, the gas sensor and the communication device are respectively connected to the power supply; the oxygen cylinder and the gas sensor are respectively connected to the second air purifier.

2. The rescue capsule of claim 1, wherein the housing comprises an inner heat-preserving layer and an outer pressure-resistant layer.

3. The rescue capsule of claim 1, wherein the gas sensor comprises a CO sensor, a $CO_2$ sensor, and a $CH_4$ sensor.

4. The rescue capsule of claim 1, wherein a switch is respectively provided between the power supply and the light, the first air purifier and the second air purifier.

5. The rescue capsule of claim 1, wherein a seat is provided at a lower portion of the passenger compartment, and the survival support device is arranged below the seat.

6. The rescue capsule of claim 1, wherein the explosion-proof sealing door is provided with a bulletproof glass window and a handle.

7. The rescue capsule of claim 1, wherein a reflective coating is coated on the external indicating sign.

8. The rescue capsule of claim 1, wherein the external indicating sign is respectively arranged on two sides of the explosion-proof sealing door of the housing, wherein the external indicating sign is an indicating arrow, and respective indicating signs of two sides of the explosion-proof sealing door are directed to the explosion-proof sealing door.

9. The rescue capsule of claim 1, wherein the rescue capsule is respectively arranged at left and right sides of a lower portion of a tunnel excavation trolley.

10. The rescue capsule of claim 1, wherein the communication device is a wireless communication device or a wired communication device; when the communication device is a wired communication device, a communication interface is provided on the housing; and the communication interface is connected to the communication device and an external communication cable outside the rescue capsule.

* * * * *